(12) United States Patent
Eversdijk

(10) Patent No.: US 9,995,656 B2
(45) Date of Patent: Jun. 12, 2018

(54) FORENSIC DEVICE FOR COLLECTING A SAMPLE

(71) Applicant: Martin Jan Peter Eversdijk, Nieuw Vennep (NL)

(72) Inventor: Martin Jan Peter Eversdijk, Nieuw Vennep (NL)

( * ) Notice: Subject to any disclaimer, the term of this patent is extended or adjusted under 35 U.S.C. 154(b) by 0 days. days.

(21) Appl. No.: 15/328,726

(22) PCT Filed: Aug. 11, 2015

(86) PCT No.: PCT/EP2015/068431
§ 371 (c)(1),
(2) Date: Jan. 24, 2017

(87) PCT Pub. No.: WO2016/023891
PCT Pub. Date: Feb. 18, 2016

(65) Prior Publication Data
US 2017/0227427 A1 Aug. 10, 2017

(30) Foreign Application Priority Data
Aug. 11, 2014 (NL) .................................... 2013316

(51) Int. Cl.
*G01N 1/02* (2006.01)
*G01N 33/48* (2006.01)
*G01N 1/00* (2006.01)

(52) U.S. Cl.
CPC ............... *G01N 1/02* (2013.01); *G01N 33/48* (2013.01); *G01N 2001/007* (2013.01)

(58) Field of Classification Search
None
See application file for complete search history.

(56) References Cited

U.S. PATENT DOCUMENTS

| | | | | |
|---|---|---|---|---|
| 3,684,660 A | * | 8/1972 | Kereluk | ................. C12M 41/36 435/305.1 |
| 6,057,151 A | * | 5/2000 | Greenwood | ............. C12N 1/04 206/204 |
| 2011/0004122 A1 | | 1/2011 | Sangha | |

(Continued)

FOREIGN PATENT DOCUMENTS

| EP | 2420318 A1 | 2/2012 |
|---|---|---|
| GB | 2430028 A | 3/2007 |

(Continued)

OTHER PUBLICATIONS

International Search Report and Written Opinion dated Nov. 30, 2015 for PCT application No. PCT/EP2015/068431 filed Aug. 11, 2015.

*Primary Examiner* — Paul West
*Assistant Examiner* — Mark A Shabman

(57) ABSTRACT

The present invention relates to a forensic device suitable for acquisition and storage of biological samples, comprising in an air tight container (1) a water soluble layer (10) which is adhered to a flexible layer (11) by a water impermeable adhesive layer (12), wherein the air tight container (1) comprises a cover (2) defining a storage compartment (3) and a base (4) having attached thereto a protrusion (5) which extends from the base (4) inside said storage compartment (3). Further, the present invention relates to the use of the forensic device to acquire and store a biological sample.

13 Claims, 2 Drawing Sheets

(56) References Cited

U.S. PATENT DOCUMENTS

Figure 1:
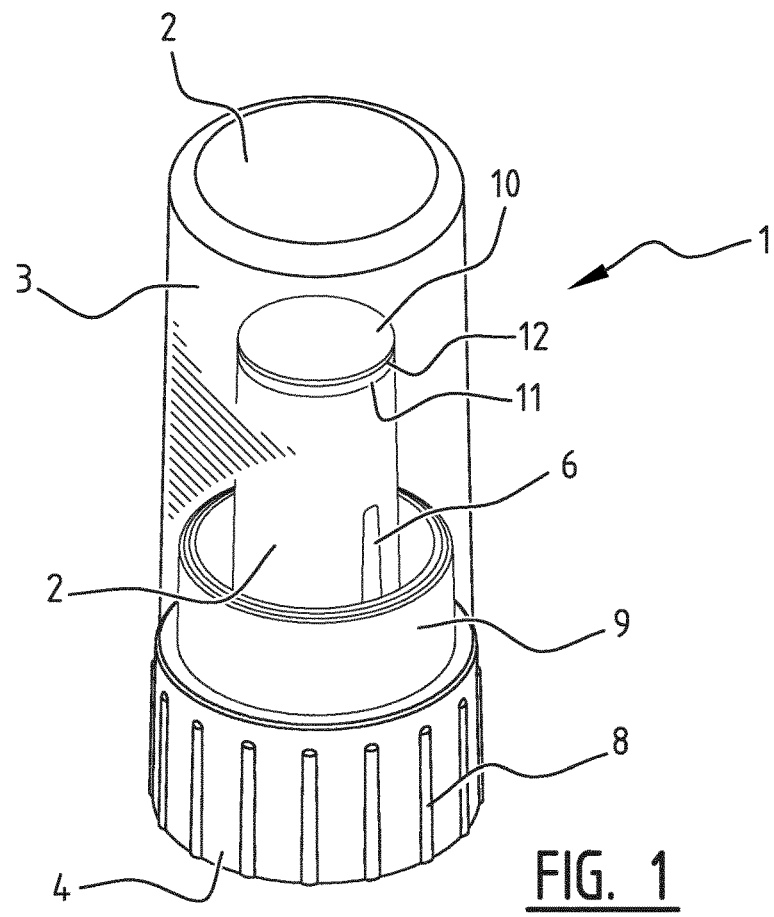

2012/0028297 A1* 2/2012 Zook .................. C12Q 1/04
                                                435/39
2013/0084897 A1* 4/2013 Zawaideh ............ H04W 4/14
                                                455/466

FOREIGN PATENT DOCUMENTS

| WO | 2009036168 A2 | 3/2009 |
| WO | 2009108229 A2 | 9/2009 |
| WO | 2011106784 A1 | 9/2011 |

* cited by examiner

FORENSIC DEVICE FOR COLLECTING A SAMPLE

The present invention relates to a forensic device which is suitable for acquisition and storage of biological samples. Further, the present invention relates to the use of a forensic device for acquisition and storage of biological samples.

In forensic investigations it is of upmost importance to gather as much as information of involved persons as is necessary or as is possible. For example, a certain critical amount of biological material needs to be safeguarded to ensure that a DNA profile could be established. In order to determine DNA profiles saliva, sperm, blood or epidermis cells are generally used as biological sample.

These biological samples are collected by touching the surface where the biological sample is placed with for example a swab. Alternatively, it is current practice to touch the surface with scotch tape in order to collect biological material. After the collection of the biological sample, the swab or scotch tape are stored to safeguard the sample.

A drawback of using a swab or scotch tape is the storage of the swab or scotch tape when the biological sample is collected. The biological sample is susceptible for degradation, for example due to growing of mold. Storage of the used swab or scotch tape to safeguard the biological sample is difficult because each handling which is carried out with the swab or scotch tape to store it may be detrimental to the quality of the DNA in the biological sample.

Another drawback of using the known methods for the collection of biological material, such as a swab or scotch tape, is that the amount of biological material which can be collected is limited. Biological material which is found in an area which is subject of forensic research may well be present on rough surfaces such as textiles or for example the roughened iron surface of a rifle. When biological material is collected from such a rough surface with a swab or with a scotch tape, the contact between the swab or scotch tape and the rough surface is not optimal. This results in that biological material which is present in small dimples is not collected. Since the amount of biological material which is present on a crime scene might be scarce, it is highly desirable to collect as much as biological material as is possible.

Given the above drawbacks of current methodologies for the collection of biological samples, there is a need in the art for a device having improved characteristics.

It is an object of the present invention, amongst other objects, to provide a forensic device providing an improved collection of biological material, or sample, and an improved storage of said material.

This objective, amongst other objectives, is met by providing a forensic device according to the appended claims.

Specifically, this object is met, amongst other objects, by providing a forensic device suitable for acquisition and storage of biological samples, comprising in an air tight container a water soluble layer which is adhered to a flexible layer by a water impermeable adhesive layer, between the water soluble layer and the flexible layer.

As used in the present context, a forensic device, or forensic stamp or alternatively a forensic stub, is a device which can be used by forensic researchers to collect and store biological material. The forensic device of the present invention, can advantageously be used for the acquisition, or alternatively, for collection, of biological samples. Especially, the present device provides an improved collection of biological sample from rough surface such as textile surfaces since the surface of the present device which contacts the rough surface, i.e. the water soluble layer, adjusts to align with the rough surface as a result of the flexible layer. Accordingly, the area of contact between the water soluble layer and the rough surface to be investigated is maximized, and thus a maximum amount of biological sample is acquired.

The present water soluble layer collects a biological sample, or biological material, whereas the present water impermeable adhesive layer avoids leakage of biological sample, or biological material, into the present flexible layer. Thus, the maximum amount of biological sample remains available in the water soluble layer. By air tightly closing the present forensic device, the device and thus the acquired biological sample can be stored before a further analysis of the sample is carried out. This provides the opportunity to collect material on a crime scene, and postpone the further analysis to a later stadium, if this research is still necessary. Accordingly, the present forensic device is a helpful tool for forensic experts to safeguard biological samples for long time periods.

According to a preferred embodiment, the present air tight container comprises a cover defining a storage compartment and a base having attached thereto a protrusion which extends from the base inside said storage compartment. Since the storage compartment is air tight the biological material which is present in the storage compartment can be stored for long time periods. Preferably the present protrusion extends into the storage compartment without contacting the present cover. Preferably the present cover is removable attached to the present base, thereby enabling opening and closing of the present forensic device.

According to yet another preferred embodiment, the present flexible layer is attached to an end surface of the present protrusion, preferably to a substantially flat end surface of the present protrusion. The end surface of the protrusion provides a safe area for storage of biological sample where the sample is not contacted by other parts of the forensic device. Further, the present base and protrusion provide an easy to handle device for the acquisition of a biological sample, since the base can easily be hold by hand, and the end surface of the protrusion of the base can be pointed towards a surface under investigation.

To guarantee tee quality of the present water soluble layer, the present water soluble layer may be protected before use by a sealing or cover which is directly attached to the water soluble layer to cover the water soluble layer, and which cover may be removed before use of the present forensic device.

In an advantageous embodiment, the present water soluble layer is provided with a color which is different from the flexible layer and/or the impermeable adhesive. When a biological sample is acquired and stored in the present water soluble layer it can easily be recovered from the water soluble layer by contacting the water soluble layer by for example a swab. To guarantee that all material from the biological sample is recovered, the present water soluble layer may have another color than the underlying water impermeable adhesive layer and underlying flexible layer. The forensic expert could easily detect whether all material from the water soluble layer, having a distinct color, is recovered or not.

In a preferred embodiment, the present flexible layer is a foam layer, preferably a polyethylene or polypropylene foam layer. Alternatively, the present flexible layer is a polyolefin foam layer, or a foam layer comprising polyolefins.

In another preferred embodiment, the present protrusion is proved with at least one passage which connects the present storage compartment with a dry compartment defined in present base. Preferably the present protrusion comprises two or at least two such as 3 or at least 3 passages which connect the present storage compartment with a dry compartment defined in present base. The advantage of the present passage is that the storage compartment wherein the biological sample is stored is in contact with a dry compartment to guarantee that the present storage compartment remains humid free. This enables the present forensic device to be used in humid climates, and still an adequate acquisition and storage of biological samples.

Preferably, the present forensic device comprises a dehumidifier, which is more preferably placed in the present dry compartment which is defined in the present base. Preferably the present dehumidifier comprises calcium chloride, silica and/or silica gel. The use of such a dehumidifier, and especially silica gel, provides an improved storability of the present forensic device, for example after a biological sample is acquired.

In a preferred embodiment, the present base is provided with projections to enable a solid grip on the base. By use of such projections, or alternatively dimples, the forensic researcher has an improved grip on the forensic device, irrespective whether the forensic researcher uses hand gloves.

In another preferred embodiment, the present base is provided with an edge, preferably an edge which abuts, or contacts, or aligns with the present cover to air tightly connect the present base with the present cover. This provides an air tight closed storage compartment for the storage of biological samples.

In a further preferred embodiment, the present forensic device comprises closing means between the present cover and the present base to air tightly close the storage compartment.

Given the beneficial properties of the present forensic device the present invention relates according to a further aspect to the use of the present forensic device for the acquisition and or storage of biological samples. Preferably, the present biological samples are forensic samples, preferably selected from saliva, sperm, blood or epidermis cells, or skin cells.

Figure 2:
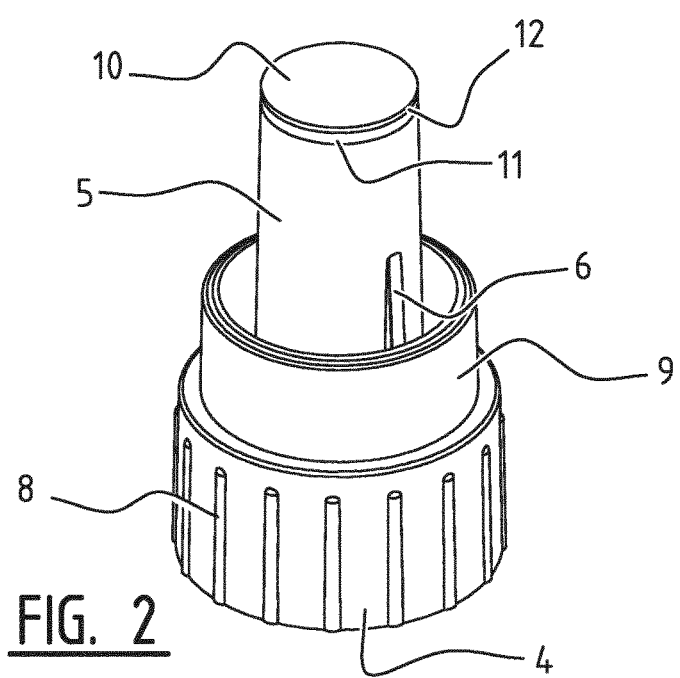
Figure 3:
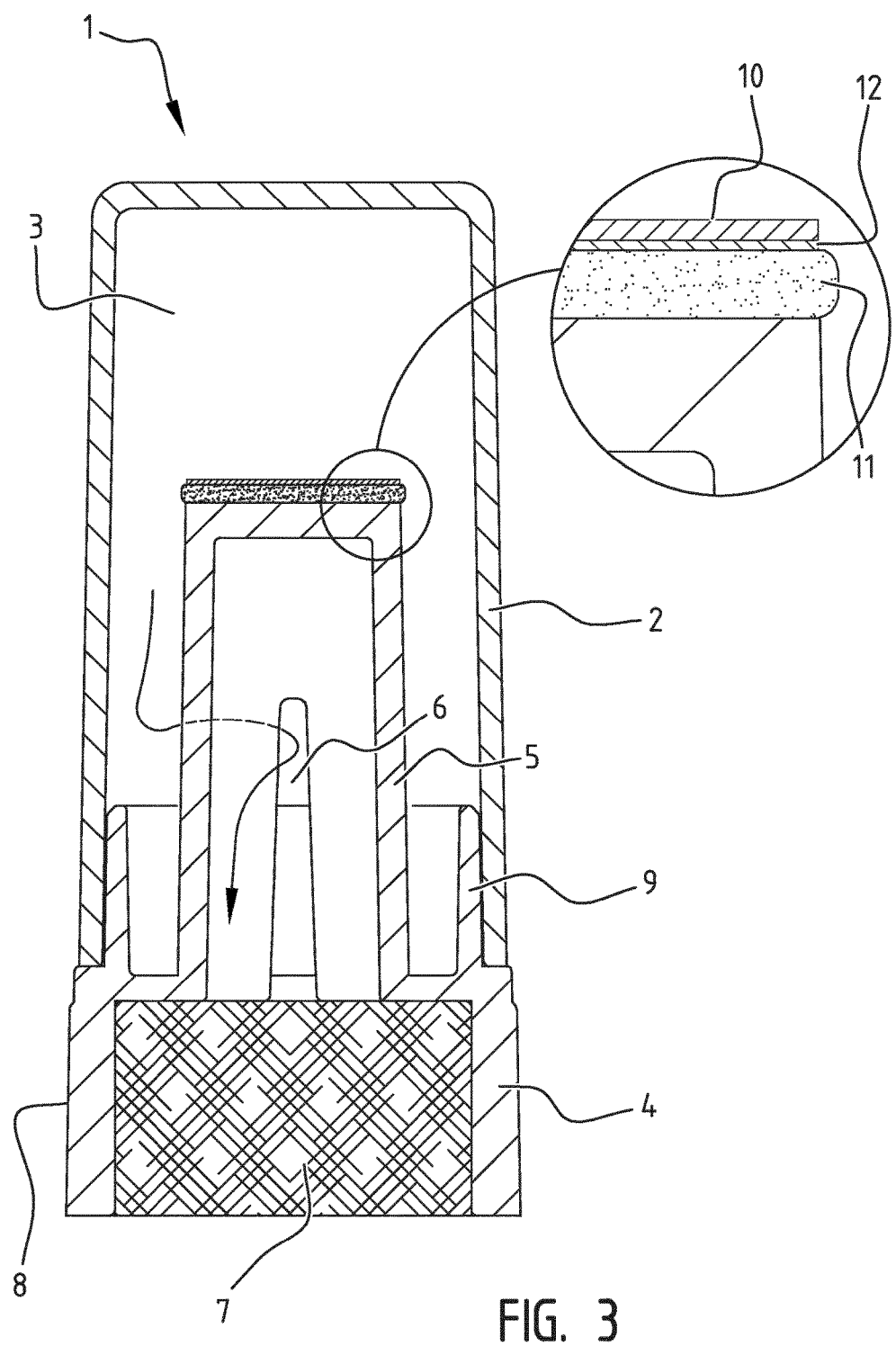

The invention is further illustrated by the below description of a preferred embodiment, wherein is referred to the FIGS. 1 to 3, showing:

FIG. 1 a perspective view of a forensic device according to the invention;

FIG. 2 a perspective view of a forensic device according to the invention wherein the cover is removed;

FIG. 3 a cross section of a forensic device according to the invention.

FIG. 1 shows forensic device of the present invention which is suitable for acquisition and storage of biological samples, comprising air tight container (1) comprising a cover (2) defining a storage compartment (3) and a base (4) having attached thereto a protrusion (5) which extends from the base (4) inside said storage compartment (3). In the shown embodiment, the forensic device is a circular device. This is advantageous for ease of handling, however, it is also possible to configure the present forensic device in another shape, such as for example rectangular. The cover (2) is air tightly connected with the base (4), and can be removed from the base (4) to use the base (4) with the protrusion (5) to acquire a biological sample such as epidermis cells from a surface. The free flat end of protrusion (5) is provided with a flexible layer (11) of polyethylene foam. On the flexible layer (11) is adhered a water soluble layer (10) having another color than the flexible layer (11) (color not shown). The water soluble layer (10) is adhered to the flexible layer (11) by a water impermeable adhesive. This provides the advantage that after the collection of the biological sample, which is acquired by the water soluble layer (10) by touching a surface with the water soluble layer (10), the water soluble layer can conveniently be separated from the adhesive layer (12) and the flexible layer (11) by wetting the water soluble layer (10) with for example water and removal of the water soluble layer by a swab.

The flexible layer (11) is advantageous for the collection of biological samples, such as for example epidermis cells, especially from rough surfaces such as clothing. The flexible layer (11) is adjustable, thus after pressing the base (4) with protrusion (5) on a rough surface, the water soluble layer (10) has a maximum contact with the rough surface to ensure that the maximum number of cells are collected by the water soluble layer (10). This is advantageous since for a further analysis, for example DNA profiling, a certain amount of biological sample needs to be present.

FIG. 1 further shows passage (6) in protrusion (5) which connects the storage compartment (3) with a dry compartment (not shown) defined in base (4). This dry compartment comprises a dehumidifier such as a dry capsule of silica gel. The passage (6) provides the advantage that the device can be stored without the degradation of the biological sample as a result of for example mold growing. Accordingly, the device of the present invention can be used on a forensic research site to acquire biological samples. After the collection of a sample it can be stored in the present device safely before the biological sample is analyzed in a research lab.

Advantageously, the cover (2) is from a transparent material, or partly transparent material, so the condition or presence of the water soluble layer (10) can be inspected without removal of the cover (2).

As is shown in FIG. 1, the base (4) provided with projections (8) to enable a solid grip on the base (4). Alternatively, the base (4) is provided with dimples to enable a solid grip.

Furthermore, base (4) is provided with circular edge (9) which outer diameter matches the inner diameter of cover (2) to ensure an air tightly connection between both parts. Advantageously, both the circular edge (9) and cover (2) are provided with closing means such as a thread.

FIG. 2 shows a forensic device as shown in FIG. 1, which is ready for the collection of biological sample because the cover (not shown) is removed. The forensic researched can conveniently grip the forensic device on base (4) and touch a certain surface to be investigated with the water soluble layer (10). The water soluble layer (10) will collect biological material such as cells by pressing the water soluble layer (10) onto the surface to be investigated. After the collection of biological sample the cover (not shown) can be air tightly placed on the base (4) for storage of the biological sample without degradation thereof.

FIG. 3 shows base (4) which defines a dry compartment (7) for containing a dry capsule. Further, base (4) is provided with circular edge (9) which outer diameter matches the inner diameter of cover (2) to ensure an air tightly connection between both parts. Cover (2) and base (4) define an air tight storage compartment (3).

The base (4) is further provided with a protrusion (5) having a passage (6) which allows an open connection between the storage compartment (3) and dry compartment (7), as indicated by the arrow. Accordingly, if any moist is present in the storage compartment (3) it may be attracted by a dry capsule present in the dry compartment (7).

Further more is shown that on the flat end surface of protrusion (5) is provided a flexible layer (11) of polyethylene foam. On the flexible layer (11) is adhered a water soluble layer (10) having another color than the flexible layer (11) (color not shown). The water soluble layer (10) is adhered to the flexible layer (11) by a water impermeable adhesive layer (12). If after collection and storage the biological sample contained in the water soluble layer (10) needs to be analyzed, the water soluble layer can be separated easily from the water impermeable adhesive layer (12) by wetting the water soluble layer and collecting the water soluble layer by a swab. Furthermore, the water impermeable adhesive layer (12) prevents leakage of biological sample into the flexible layer (11) in case the biological sample is collected from a humid surface and/or a wet biological sample.

The invention claimed is:

1. A forensic device for acquisition and storage of forensic biological samples, comprising:
    an air tight container comprising a cover defining a storage compartment, and a base having attached thereto a protrusion which extends from the base into the interior of said storage compartment, said protrusion having an end surface extending inside the interior of said storage compartment, and wherein a flexible layer extending inside the interior of said storage compartment is attached to said end surface of said protrusion, and wherein a water soluble layer extending inside the interior of said storage compartment is adhered to the flexible layer by a water impermeable adhesive layer.

2. The forensic device according to claim 1, wherein the water soluble layer is provided with a sealing.

3. The forensic device according to claim 1, wherein the water soluble layer is provided with a color which is different from a color of at least one of the flexible layer and the water impermeable adhesive layer.

4. The forensic device according to claim 1, wherein the flexible layer is a foam layer.

5. The forensic device according to claim 4, wherein the flexible layer is a polyethylene foam layer.

6. The forensic device according to claim 1, wherein the protrusion is provided with at least one passage which connects the storage compartment with a dry compartment defined in the base.

7. The forensic device according to claim 1, further comprising a dehumidifier.

8. The forensic device according to claim 7, wherein the dehumidifier is placed in a dry compartment defined in the base.

9. The forensic device according to claim 1, wherein the base is provided with projections to enable a grip on the base.

10. The forensic device according to claim 1, wherein the base is provided with an edge which abuts the cover to air tightly connect the base with the cover.

11. The forensic device according to claim 1, further comprising closing means between the cover and the base to air tightly close the storage compartment.

12. A method of using the forensic device as defined in claim 1, comprising:
    using the forensic device for at least one of acquisition and storage of forensic biological samples.

13. The method of claim 12, wherein the forensic samples are selected from the list consisting of saliva, sperm, blood and epidermis cells.

* * * * *